(12) United States Patent
Madsen et al.

(10) Patent No.: US 6,698,424 B2
(45) Date of Patent: Mar. 2, 2004

(54) MEDICAL CONNECTOR FOR A RESPIRATORY ASSEMBLY

(75) Inventors: Edward B. Madsen, Riverton, UT (US); David M. Cise, Herriman, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 71 days.

(21) Appl. No.: 10/036,748

(22) Filed: Dec. 21, 2001

(65) Prior Publication Data

US 2003/0116162 A1 Jun. 26, 2003

(51) Int. Cl.$^7$ .................................................. A62B 9/04
(52) U.S. Cl. ................................................ 128/202.27
(58) Field of Search .......................... 128/202.27, 912, 128/207.16; 285/394, 396

(56) References Cited

U.S. PATENT DOCUMENTS

| | | |
|---|---|---|
| 2,820,651 A | 1/1958 | Phillips |
| 3,461,877 A | 8/1969 | Morch |
| 3,552,778 A | 1/1971 | Muller |
| 4,009,720 A | 3/1977 | Crandall |
| 4,029,105 A | 6/1977 | Faust |
| 4,033,353 A | 7/1977 | La Rosa |
| 4,152,017 A | 5/1979 | Abramson |
| 4,254,773 A | 3/1981 | Waldbillig |
| 4,351,328 A | 9/1982 | Bodai |
| 4,369,991 A | 1/1983 | Linder |
| 4,406,485 A | 9/1983 | Giebeler |
| 4,416,273 A | 11/1983 | Grimes |
| 4,432,759 A | 2/1984 | Gross et al. |
| 4,510,933 A | 4/1985 | Wendt et al. |
| 4,521,038 A | 6/1985 | Cerny |

(List continued on next page.)

FOREIGN PATENT DOCUMENTS

| | | |
|---|---|---|
| DE | 3339988 | 5/1985 |
| EP | 0151519 | 8/1985 |
| EP | 0462412 | 12/1991 |
| EP | 0700687 | 3/1996 |
| EP | 1157714 | 11/2001 |
| GB | 2007789 | 5/1979 |
| WO | WO8000307 | 3/1980 |
| WO | 9101120 | 2/1991 |
| WO | WO0024439 | 5/2000 |

OTHER PUBLICATIONS

International Search Report, Jan. 22, 2003.

U.S. patent application, Ser. No. 09/680,125 (BAL–71 (15799)), Filed Oct. 5, 2000.

English language Abstract of DE 33 39 988 A1, Derwent Info. Ltd. © 2002.

Primary Examiner—Henry Bennett
Assistant Examiner—Sabrina Dagostino
(74) Attorney, Agent, or Firm—Dority & Manning, P.A.

(57) ABSTRACT

A connection assembly for use with a respiratory circuit assembly is provided. The connection assembly includes a first connection member that has an opening therethrough to allow for the transport of fluids and objects through the first connection member. The first connection member has a recess on an end thereof. A second connection member is present that is releaseably engageable with the first connection member. The second connection member has an opening therethrough to allow for the transport of fluids and objects through the second connection member. The second connection member has a disconnect member that is engageable within the recess. A snap fit member may be present on at least one of the first and second connection members. The snap fit member hinders unintentional disengagement of the first and second connection members. Relative movement between the first connection member and the disconnect member causes a separation of the first and second connection members.

21 Claims, 4 Drawing Sheets

U.S. PATENT DOCUMENTS

| | | |
|---|---|---|
| 4,551,146 A | 11/1985 | Rogers |
| 4,557,261 A | 12/1985 | Rugheimer |
| 4,610,469 A | 9/1986 | Wolff-Mooij |
| 4,612,929 A | 9/1986 | Schubert et al. |
| 4,676,241 A | 6/1987 | Webb et al. |
| 4,774,940 A | 10/1988 | Linder |
| 4,787,655 A | 11/1988 | Gross et al. |
| 4,796,615 A | 1/1989 | Bullock et al. |
| 4,827,921 A | 5/1989 | Rugheimer |
| 4,893,848 A | 1/1990 | Melcher |
| 4,909,248 A | 3/1990 | McLennan Anderson |
| 4,979,765 A | 12/1990 | Bartholomew |
| 5,054,482 A | 10/1991 | Bales |
| 5,062,420 A | 11/1991 | Levine |
| 5,140,983 A | 8/1992 | Jinotti |
| 5,158,569 A | 10/1992 | Strickland et al. |
| 5,184,611 A | 2/1993 | Turnbull |
| 5,213,095 A | 5/1993 | Dague |
| 5,220,916 A | 6/1993 | Russo |
| 5,222,486 A | 6/1993 | Vaughn |
| 5,230,332 A | 7/1993 | Strickland |
| 5,251,617 A | 10/1993 | Linder |
| 5,255,676 A | 10/1993 | Russo |
| 5,259,376 A | 11/1993 | Bales |
| 5,263,478 A | 11/1993 | Davis |
| 5,284,134 A * | 2/1994 | Vaughn et al. ......... 128/200.24 |
| 5,333,606 A | 8/1994 | Schneider et al. |
| 5,333,608 A | 8/1994 | Cummins |
| 5,355,876 A | 10/1994 | Brodsky et al. |
| 5,361,754 A | 11/1994 | Stuart |
| 5,370,610 A | 12/1994 | Reynolds |
| 5,390,669 A | 2/1995 | Stuart et al. |
| 5,445,141 A | 8/1995 | Kee et al. |
| 5,476,291 A | 12/1995 | Reneau |
| 5,509,911 A | 4/1996 | Cottone, Sr. et al. |
| 5,513,633 A | 5/1996 | Islava |
| 5,527,299 A | 6/1996 | Cude |
| 5,549,583 A | 8/1996 | Sanford et al. |
| 5,620,426 A | 4/1997 | Braithwaite |
| 5,642,726 A | 7/1997 | Owens et al. |
| 5,694,922 A | 12/1997 | Palmer |
| 5,720,282 A | 2/1998 | Wright |
| 5,730,123 A | 3/1998 | Lorenzen et al. |
| 5,735,271 A | 4/1998 | Lorenzen et al. |
| 5,772,255 A | 6/1998 | Osborne et al. |
| 5,775,325 A | 7/1998 | Russo |
| 5,778,877 A | 7/1998 | Stuart |
| 5,820,614 A * | 10/1998 | Erskine et al. .............. 604/533 |
| 5,830,195 A | 11/1998 | Peters et al. |
| 5,855,230 A | 1/1999 | Guala et al. |
| 5,882,348 A | 3/1999 | Winterton et al. |
| 5,971,958 A * | 10/1999 | Zhang .................. 604/165.02 |
| 6,012,451 A | 1/2000 | Palmer |
| 6,095,505 A | 8/2000 | Miller |
| 6,109,259 A | 8/2000 | Fitzgerald |
| 6,135,111 A | 10/2000 | Mongeon |
| 6,248,099 B1 | 6/2001 | Bell |

* cited by examiner

MEDICAL CONNECTOR FOR A RESPIRATORY ASSEMBLY

BACKGROUND

Endotracheal intubation is a common procedure in the field of respiratory medical care. Endotracheal intubation tubes are used in many situations for providing artificial airways for passage of respiratory gasses and medical procedure devices to patients. For instance, endotracheal tubes may be used to insert a catheter therethrough in order to clean lung secretions from a patient. Endotracheal tubes may be used in situations where patients have stopped independent breathing and are required to be supported on a ventilator. In addition, endotracheal tubing may be used for other procedures such as: oxygenation of the lungs; elimination or reduction of residual carbon dioxide from the lungs; visual inspection of portions of the respiratory system; sampling sputum and gasses; measuring parameters such as flow rates, pressure, and temperature of gasses within the respiratory system; and/or the administration of medication, gasses, and/or lavage.

All of these procedures require various instruments to be used in conjunction with the respiratory circuit. In addition, other equipment may be incorporated into the circuit. For example, some respiratory circuits include a humidifier. Humidifiers are advantageous because breathing gasses supplied to a patient must be warm and humidified in order to provide quality inhalation therapy. A humidifier is typically connected in the breathing circuit between the ventilator and the patient. Air from the ventilator is warmed and moisturized by the humidifier and then is supplied to the patient. Due to the fact that various instruments and pieces of equipment must be connected and reconnected to the respiratory circuit, connectors are often employed in such circuits.

Connectors are often permanently bonded to instruments and manifolds in respiratory circuits. This type of attachment is advantageous because a secure and fluid-tight fit is provided. However, permanently bonding an instrument or other piece of equipment in a respiratory circuit has inherent disadvantages. For instance, an instrument that is permanently bonded to a connector cannot be removed therefrom and must be replaced oftentimes increasing the cost of the medical treatment. Further, permanently bonding a diagnostic instrument to a connector may prevent the clinician from performing some other type of procedure on the patient during ventilation of the patient. Additionally, damage of an instrument or piece of equipment that is permanently bonded to a connector may necessitate the replacement of several components of the respiratory circuit.

Connectors which are detachable have been used in order to overcome the problems associated with permanently bonded connectors in respiratory circuits. A detachable connector allows for various instruments and pieces of equipment to be interchanged in a respiratory breathing circuit. As such, the respiratory breathing circuit can be configured to provide for an increased number of procedures. Additionally, the ability to remove instruments from the breathing apparatus may allow for the instrument to be cleaned, hence reducing the costs associated with the procedure.

However, problems with disconnect medical connectors do exist. Typically, such connectors are interference-fit connectors. For instance, a fitting on a catheter may be connected to a complimentary fitting on a manifold of a respiratory breathing circuit by forcing one fitting onto the other. The catheter is then held onto the manifold via an interference fit between the two fittings. Since the connection is not a permanent connection, air or other fluids may leak through this interference-fit connection. Additionally, if the fittings of interference-fit connectors are not adequately pressed against one another, forces could act on the connection to accidentally disconnect the connection. Obviously, such a result is unacceptable. Also, multiple fittings which are connected together via an interference fit may sometimes be difficult for a doctor or caregiver to disconnect when it is necessary to remove the surgical instrument. One example of an interference-fit connector is shown in U.S. Pat. No. 5,820,614.

The present invention improves the general type of medical connectors currently employed, and further addresses the need in the medical field for an improved medical connector for use with a respiratory breathing circuit.

SUMMARY

Objects and advantages of the invention will be set forth in part in the following description, or may be obvious from the description, or may be learned through practice of the invention.

The present invention provides for a connection assembly that is used with a respiratory circuit assembly. The connection assembly includes a cylindrical first connection member that has a bore therethrough. The first connection member is configured for engagement with a first respiratory circuit member and allows for transport of fluids and objects therethrough. The first connection member has a locking member that is located thereon for engagement with a second connection member to prevent disengagement between the first and second connection members. In one embodiment, this locking member includes a recess on one end of the first connection member. A portion of the recess defines at least one ramp on the first connection member.

A second connection member is present that has a cylindrical body with a bore therethrough. The second connection member allows for the transport of fluids and objects therethrough, and is configured for engagement with a second respiratory circuit member. The second connection member has a disconnect member with a curved surface at least where the disconnect member is located in the recess during engagement between the locking member and the first connection member. Relative rotation between the first connection member and the second connection member causes the curved surface to move along the ramp. This effects disengagement of the locking member and the first connection member, and causes separation of the first and second connection members.

The present invention also includes a connection assembly as immediately discussed where the disconnect member is a cylindrical irrigation port.

Further, the present invention includes a connection assembly as previously discussed where the locking member includes a locking ring that substantially surrounds the circumference of the first connection member. The locking ring is located proximate to the recess of the first connection member. The second connection member has a groove for engaging the locking ring and acting with the locking ring to prevent disengagement between the second connection member and the first connection member.

The present invention also includes a connection assembly as immediately discussed where the disconnect member has at least part of the surface being curved where the disconnect member engages along the ramped surface.

Further included in the present invention is a connection assembly as previously discussed where the disconnect member is a substantially cylindrical irrigation port.

Further included in the present invention is an exemplary embodiment as previously discussed where the locking member is at least one barb located on one of the first and second connection members.

In one embodiment of the connection assembly, a snap fit member is present on at least one of the first and second connection members. The snap fit member hinders unintentional disengagement of the first and second connection members. Relative movement between the first connection member and the disconnect member motivates a separation of the first and second connection members.

Further included in the present invention is an exemplary embodiment as previously mentioned where the snap fit member is at least one barb located on the second connection member.

Additionally, the present invention includes an embodiment as previously discussed where the snap fit member is a locking ring that substantially surrounds the first connection member. The second connection member has a groove for receiving the locking ring to hinder disengagement of the first and second connection members.

BRIEF DESCRIPTION OF THE DRAWINGS

An embodiment of the present invention is described by way of example with reference to the accompanying drawings, in which.

DETAILED DESCRIPTION

Figure 1:
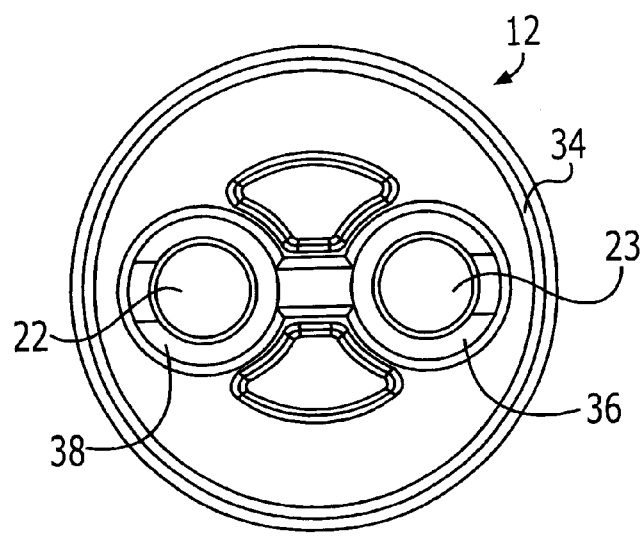
FIG. 1 is a bottom plan view of an exemplary embodiment of a first connection member in accordance with the present invention. The drawing shows two ports located on a rotatable manifold.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Figure 2:
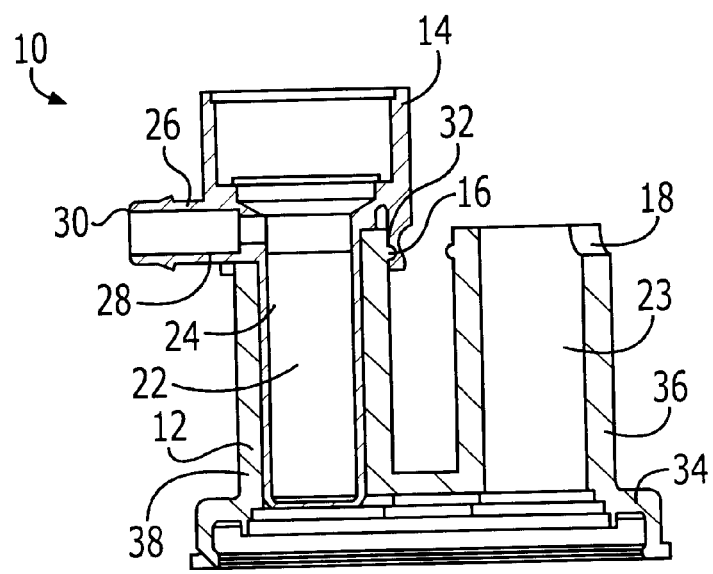
FIG. 2 is a cross-sectional elevation view of an exemplary embodiment of a connection assembly in accordance with the present invention. The drawing shows a first connection member engaged with a second connection member by use of a locking member.

An exemplary embodiment of a connection assembly 10 is shown in FIG. 2. The connection assembly 10 includes a first connection member 12 that is engaged with a second connection member 14. The connection assembly 10 is designed to include both a positive locking engagement between the first and second connection members 12 and 14 along with a way of disengaging the locking arrangement by rotating the first and second connection members; 12 and 14 relative to one another. Such an arrangement is advantageous because the connection assembly 10 will only be disengaged when desired by a user, and not disengaged by accident. Additionally, relative rotation between the first and second connection members 12 and 14 provides for a way of disengaging the connection assembly 10 without requiring a user to exert substantial force.

The first connection member 12 is shown in FIG. 2 as being a rotatable manifold 34. The rotatable manifold 34 may be incorporated into a respiratory circuit in order to permit access to the respiratory circuit through various ports. The rotatable manifold 34 shown in FIG. 2 has two ports 36 and 38 located thereon. In other exemplary embodiments of the present invention, the rotatable manifold 34 may be supplied as the first connection member 12 with a varying number of ports located thereon. Additionally, other exemplary embodiments of the present invention include a first connection member 12 that has only one port located thereon. A rotatable manifold 34 is known from U.S. Pat. No. 5,735,271 which is assigned to the assignee of the current application and is incorporated herein for all purposes in its entirety. The rotatable manifold 34 allows for the access of the respiratory circuit by a medical caregiver through different ports which may be sized and configured to accept various medical instruments and fluids. Other exemplary embodiments exist where the connection assembly 10 is not incorporated with a rotatable manifold 34, but incorporated with other components of the respiratory circuit.

Shown engaged with the first connection member 12 in FIG. 2 is the second connection member 14. The connection between the first and second connection members 12 and 14 is effected by a groove 32 and locking member 16. The locking member 16 is located on one end of port 38 of the first connection member 12. The locking member 16 is simply a projection that extends substantially around the circumference of the port 38. Groove 32 is located substantially around the circumference of a section of the second connection member 14. The groove 32 and the locking member 16 are sized in such a way that engagement between the two causes a "snap-fit" connection. This connection prevents the first and second connection members 12 and 14 from separating from one another during normal use of the respiratory circuit. Therefore, the connection assembly 10 will not become disengaged during normal use, and will only become disengaged when desired by a medical caregiver.

FIG. 1 is a bottom plan view of a first connection member 12 being a rotatable manifold 34 with two ports 36 and 38 located thereon. A first opening of the connection member 22 and a second opening of the first connection member 23 are located through ports 36 and 38. These openings 22 and 23 allow for the transport of fluids and medical devices into and out of the respiratory circuit. It is to be understood that in the present application, the word "port" is defined to be a member that has an opening therethrough. Both the opening and the member can be of any shape. The member is configured to allow for the passage of fluids and/or medical devices to and from the respiratory circuit.

Figure 3:
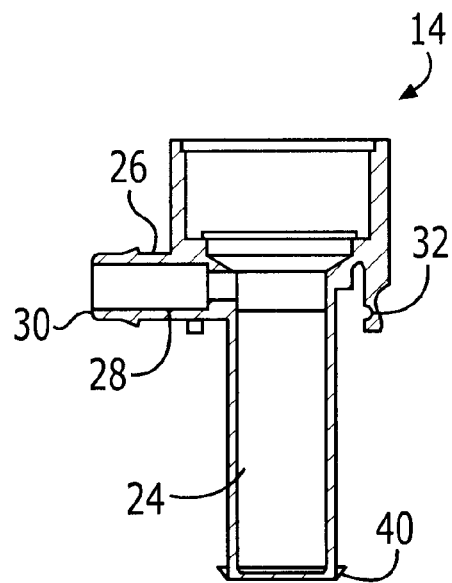
FIG. 3 is a cross-sectional elevational view of an exemplary embodiment of the second connection member in accordance with the present invention. The drawing shows a barb located on one end of the second connection member.
Figure 4:
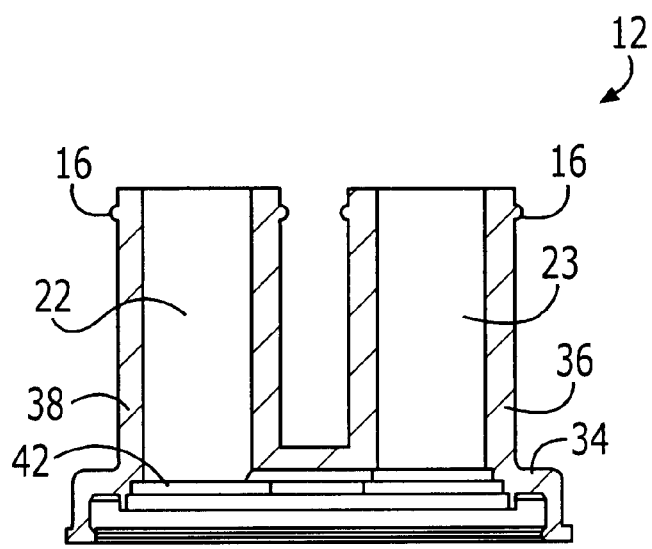
FIG. 4 is a cross-sectional elevation view of an exemplary embodiment of the first connection member in accordance with the present invention. The drawing shows the rotatable manifold having two ports with locking members on both of the ports.

FIG. 3 shows an exemplary embodiment of a second connection member in accordance with the present invention. Here, a barb 40 is located on one end of the second connection member 14. The barb 40 is designed to engage a barb locking surface 42 of the first connection member 12 as shown in FIG. 4. In this exemplary embodiment, insertion of the second connection member 14 into the opening of the first connection member 22 causes the barb 40 to be compressed. Once the barb 40 clears the length of the first opening of the first connection member 22, the barb 40 snaps into place onto the barb locking surface 42. This in effect causes a positive locking connection between the first and second connection members 12 and 14. This arrangement can be thought of as a "snap-fit" connection. The use of a barb 40 to effect the locking of the connection assembly 10 may be substituted for or used in addition to the use of a locking member 16 in combination with a groove 32 to effect the locking of the connection assembly 10. As such, exemplary embodiments of the present invention may include exemplary embodiments that include only a barb 40, a locking member 16, or both locking member 16 and barb 40. Additionally, other exemplary embodiments of the present invention may include members that form a positive locking arrangement between the first and second connection members 12 and 14 that are known in the art.

Figure 7:
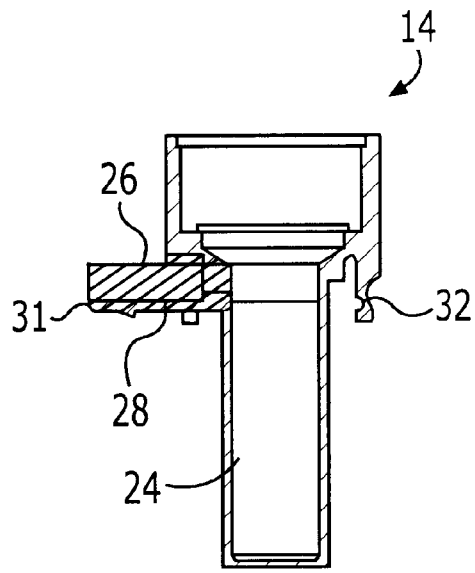
FIG. 7 is a cross-sectional elevational view of an exemplary embodiment of the second connection member in accordance with the present invention. The second connection member is shown having a semi-cylindrical lug.
Figure 8:
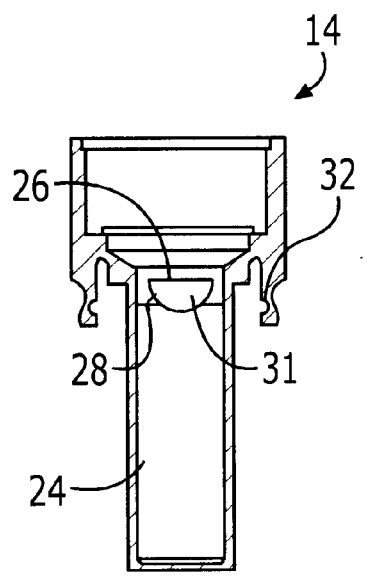
FIG. 8 is a side view of the exemplary embodiment of the second connection member shown in FIG. 7.

In order to disengage the first connection member 12 from the second connection member 14, a disconnect member 26 is provided. The exemplary embodiments shown in FIGS. 2 and 3 show a disconnect member 26 that is a irrigation port 30 having a cylindrical surface 28. In other exemplary embodiments of the present invention, only a semi-cylindrical surface 28 is present. Additionally, other exemplary embodiments of the present invention include a disconnect member 26 that has only a partially curved surface. Also, the disconnect member 26 does not have to be an irrigation port 30, but may simply be a lug or other member. For instance, FIGS. 7 and 8 show an exemplary embodiment of the present invention where the disconnect member 26 is a semi-cylindrical lug 31. An advantage of using the irrigation port 30 as the disconnect member 26 is that the irrigation port 30 may be used for another function such as the introduction of lavage into the respiratory circuit.

Figure 5:
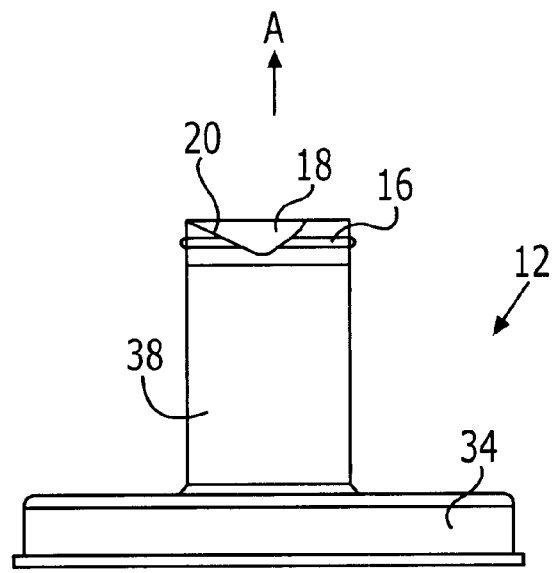
FIG. 5 is an elevation view of an exemplary embodiment of a first connection member in accordance with the present invention. The drawing shows a recess defining a ramp on one end of the first connection member and proximate to the locking member.

FIG. 5 shows an exemplary embodiment of the first connection member 12 in accordance with the present invention. More particularly, FIG. 5 shows a recess 18 being located on one end of a port 38 of the rotatable manifold 34. Recess 18 is curved in order to receive the cylindrical surface 28 of the second connection member 14 of FIG. 3. Additionally, recess 18 in FIG. 5 defines a ramp 20. In the exemplary embodiment shown in FIG. 5, ramp 20 extends to the end of the port 38. The locking member 16 is a locking ring that substantially surrounds port 38, but does not completely surround port 38. The locking member 16 is interrupted in the vicinity of the recess 18. During engagement between the first and second connection members 12 and 14, the disconnect member 26 is inserted into the recess 18, and seats against the port 38. Recess 18 is sized and shaped in order to accept the cylindrical surface 38 of the irrigation port 30. Groove 32 is fit around the locking member 16 and the combination of the two securely holds the first and second connection members 12 and 14 against one another.

To disengage the connection assembly 10, a user will rotate the first and second connection members 12 and 14 with respect to one another such that the disconnect member 26 is pushed against the ramp 20. The cylindrical surface 28 of the irrigation port 30 is then urged against ramp 20 and moves against ramp 20. This movement results in a force that has a component in the direction of arrow A in FIG. 5. This force then causes the locking member 16 to be disengaged from the groove 32 and allows the first connection member 12 to be removed from the second connection member 14.

As such, the exemplary embodiment shown in FIG. 5 has a first connection member 12 that is disengaged from the second connection member 14 upon clockwise rotation of the second connection member 14 with respect to the first connection member 12. However, other exemplary embodiments of the present invention exist where the ramp 20 is positioned opposite to the position shown in FIG. 5 such that the first connection member 12 is disengaged via counterclockwise rotation of the second connection member 14. In addition, other exemplary embodiments exist where the recess 18 defines two ramps 20 on the port 38 of the rotatable manifold 34. Here, a user can disengage the first and second connection members 12 and 14 by rotating them relative to one another in either direction.

Figure 6:
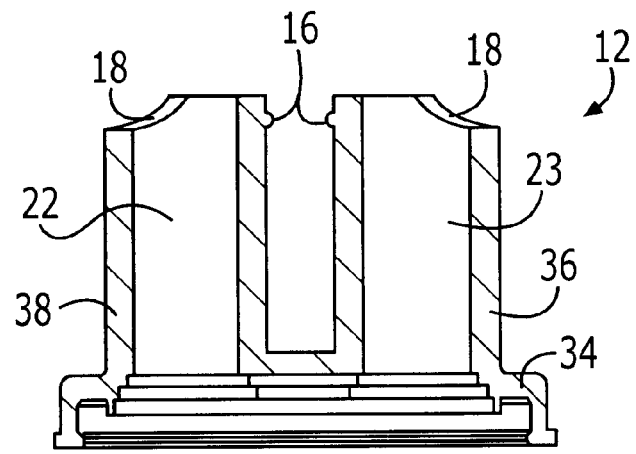
FIG. 6 is a cross-sectional elevation view of an exemplary embodiment of a first connection member in accordance with the present invention. The drawing shows a rotatable manifold having two ports with locking members and recesses on both of the ports.

FIG. 6 shows another exemplary embodiment of the present invention where a first connection member 12 has two ports 36 and 38 both having a locking member 16 and a recess 18 defined on one end. As such, the connection assembly 10 may be included in all of the ports of the rotatable manifold 34 and not only on a single port of the rotatable manifold 34.

Additionally, the fit between the first and second connection members 12 and 14 may be tight enough in other exemplary embodiments of the present invention such that a seal is formed between the first and second connection members 12 and 14. A taper may be provided on one of the connection members 12 and 14 to effect this seal in other exemplary embodiments.

It should be understood that the invention includes various modifications that can be made to the exemplary embodiments of the medical connector for a respiratory circuit as described herein as come within the scope of the appended claims and their equivalents.

What is claimed is:

1. A connection assembly for use with a respiratory circuit assembly, comprising:

a first connection member and a second connection member;

said first connection member being generally cylindrical and having a bore therethrough, said first connection member allowing for transport of fluids and objects therethrough, said first connection member having a locking member located thereon for engagement with said second connection member to prevent disengagement between said second connection member and said first connection member, said first connection member having a recess on one end, a portion of said recess defining at least one ramp, said first connection member being configured for engagement with a first respiratory circuit member; and said second connection member having a cylindrical body with a bore therethrough, said second connection member allowing for the transport of fluids and objects therethrough, said second connection member being configured for engagement with a second respiratory circuit member, said second connection member having a disconnect member with a curved surface at least where said disconnect member is located in said recess during engagement between said locking member and said second connection member, wherein during engagement between said locking member and said second connection member said locking member prevents relative axial movement between said first connection member and said second connection member, wherein relative rotation between said first connection member and said second connection member causes said curved surface to move along said ramp to effect disengagement of said locking member and said first connection member and causes separation of said first connection member and said second connection member.

2. A connection assembly for use with a respiratory circuit assembly, comprising:

a first connection member and a second connection member;

said first connection member being generally cylindrical and having a bore therethrough, said first connection member allowing for transport of fluids and objects therethrough, said first connection member having a locking member located thereon for engagement with said second connection member to prevent disengagement between said second connection member and said first connection member, said first connection member having a recess on one end, a portion of said recess defining at least one ramp, said first connection member being configured for engagement with a first respiratory circuit member; and said second connection member having a cylindrical body with a bore therethrough, said second connection member allowing for the transport of fluids and objects therethrough, said second connection member being configured for engagement with a second respiratory circuit member, said second connection member having a disconnect member with a curved surface at least where said disconnect member is located in said recess during engagement between said locking member and said second connection member, wherein relative rotation between said first connection member and said second connection member causes said curved surface to move along said ramp to effect disengagement of said locking member and said first connection member and causes separation of said first connection member and said second connection member, wherein said disconnect member is a cylindrical irrigation port.

3. A connection assembly for use with a respiratory circuit assembly, comprising:

a first connection member and a second connection member;

said first connection member being generally cylindrical and having a bore therethrough, said first connection member allowing for transport of fluids and objects therethrough, said first connection member having a locking member located thereon for engagement with said second connection member to prevent disengagement between said second connection member and said first connection member, said first connection member having a recess on one end, a portion of said recess defining at least one ramp, said first connection member being configured for engagement with a first respiratory circuit member; and said second connection member having a cylindrical body with a bore therethrough, said second connection member allowing for the transport of fluids and objects therethrough, said second connection member being configured for engagement with a second respiratory circuit member, said second connection member having a disconnect member with a curved surface at least where said disconnect member is located in said recess during engagement between said locking member and said second connection member, wherein relative rotation between said first connection member and said second connection member causes said curved surface to move along said ramp to effect disengagement of said locking member and said first connection member and causes separation of said first connection member and said second connection member, wherein said disconnect member is a semi-cylindrical lug.

4. The connection assembly of claim 1, wherein said locking member is a locking ring that substantially surrounds the circumference of said first connection member, said locking ring is located proximate to said recess of said first connection member, wherein said second connection member has a groove for engaging said locking ring and acting with said locking ring to prevent disengagement between said second connection member and said first connection member.

5. The connection assembly of claim 1, wherein said recess of said first connection member defines two ramps.

6. The connection assembly of claim 1, wherein the first connection member is a rotatable manifold having at least two ports, and wherein the second connection member is an aspirating catheter assembly.

7. The connection assembly of claim 1, wherein one of said first connection member and said second connection member has a tapered surface to create a seal between said first and second connection members.

8. A connection assembly for use with a respiratory circuit assembly, comprising:

a first connection member having an opening therethrough to allow for the transport of fluids and objects through said first connection member, said first connection member having a recess on one end, said recess defining at least one ramped surface;

a second connection member having an opening therethrough to allow for the transport of fluids and objects through said second connection member, said second connection member engageable with said first connection member and having a disconnect member engageable within said recess;

a locking member configured on at least one of said first connection member and said second connection member, said locking member preventing relative axial movement between said first and second connection members when said first and second connection members are engaged with one another; and wherein rotational movement of said disconnect member along said ramp effects disengagement of said locking member and separation of said first and second connection members.

9. The connection assembly of claim 8, wherein said disconnect member has at least part of the surface of said disconnect member being curved, where said disconnect member engages along said ramped surface.

10. A connection assembly for use with a respiratory circuit assembly, comprising:

a first connection member having an opening therethrough to allow for the transport of fluids and objects through said first connection member, said first connection member having a recess on one end, said recess defining at least one ramped surface;

a second connection member having an opening therethrough to allow for the transport of fluids and objects through said second connection member, said second connection member engageable with said first connection member and having a disconnect member engageable within said recess;

a locking member configured on at least one of said first connection member and said second connection member, said locking member preventing disengagement of said first and second connection members when said first and second connection members are engaged with one another; and wherein rotational movement of said disconnect member along said ramp effects disengagement of said locking member and separation of said first and second connection members, wherein said disconnect member is a substantially cylindrical irrigation port.

11. The connection assembly of claim 8, wherein said locking member is a locking ring, during at least engagement of said first and second connection members said locking ring is proximate to said recess of said first connection member.

12. The connection assembly of claim 8, wherein:

said locking member is configured on said first connection member, said locking member is a locking ring that substantially surrounds said first connection member, said locking ring is proximate to said recess of said first connection member; and wherein said second connection member has a groove for receiving said locking ring, said groove and said locking ring act to prevent disengagement of said first and second connection members when said first and second connection members are engaged with one another.

13. The connection assembly of claim 8, wherein said locking member is at least one barb located on one of said first and second connection members.

14. The connection assembly of claim 8, wherein said disconnect member is a lug having at least a partially curved surface where said disconnect member engages along said ramped surface.

15. The connection assembly of claim 9, wherein said disconnect member is a substantially cylindrical irrigation port.

16. The connection assembly of claim 8, wherein one of said first connection members and said second connection member has a tapered surface to create a seal between said first and second connection members.

17. A connection assembly for use with a respiratory circuit assembly, comprising:

a first connection member having an opening therethrough to allow for the transport of fluids and objects through said first connection member, said first connection member having a recess defining at least one ramped surface;

a second connection member releaseably engageable with said first connection member and having an opening therethrough to allow for the transport of fluids and objects through said second connection member, said second connection member having a disconnect member engageable within said recess;

a snap fit member on at least one of said first and second connection members, said snap fit member preventing relative axial movement between said first and second connection members when said first and second connection members are engaged with one another; and wherein relative movement between said first connection member and said disconnect member motivates a separation of said first and second connection members.

18. The connection assembly of claim 17, wherein said recess defines at least one ramped surface and wherein said disconnect member slides on said ramped surface upon engagement and disengagement of said connection members.

19. The connection assembly of claim 17, wherein said snap fit member is at least one barb located on said second connection member.

20. The connection assembly of claim 17, wherein said snap fit member is a locking ring that at least substantially surrounds the first connection member, and wherein said second connection member has a groove for receiving said locking ring to hinder disengagement of said first and second connection members.

21. A connection assembly for use with a respiratory circuit assembly, comprising:

a first connection member having an opening therethrough to allow for the transport of fluids and objects through said first connection member, said first connection member having a recess;

a second connection member releaseably engageable with said first connection member and having an opening therethrough to allow for the transport of fluids and objects through said second connection member, said second connection member having a disconnect member engageable within said recess;

a snap fit member on at least one of said first and second connection members, said snap fit member preventing unintentional disengagement of said first and second connection members; and wherein relative movement between said first connection member and said disconnect member motivates a separation of said first and second connection members, wherein said disconnect member is a substantially cylindrical irrigation port.

* * * * *